United States Patent [19]

Schallner et al.

[11] 4,338,262
[45] Jul. 6, 1982

[54] CARBOXYLIC ACID DERIVATIVES

[75] Inventors: Otto Schallner; Siegfried Oeckl, both of Cologne; Karl H. Schündehütte, Leverkusen, all of Fed. Rep. of Germany

[73] Assignee: Bayer Aktiengesellschaft, Leverkusen, Fed. Rep. of Germany

[21] Appl. No.: 180,275

[22] Filed: Aug. 21, 1980

[30] Foreign Application Priority Data

Sep. 4, 1979 [DE] Fed. Rep. of Germany ....... 2935682

[51] Int. Cl.³ .................. C07C 147/02; C07C 147/06
[52] U.S. Cl. ............................. 260/544 S; 260/544 F; 260/544 Y; 260/546
[58] Field of Search ................ 260/544 S, 546, 544 Y, 260/544 F; 562/429

[56] References Cited

U.S. PATENT DOCUMENTS 3,140,306  7/1964  Heiniger ............................. 260/464
3,225,085 12/1965  Eby ....................................... 560/17

FOREIGN PATENT DOCUMENTS 1452174 10/1976 United Kingdom .

OTHER PUBLICATIONS

Lin'kova, M. G., *Chemical Abstracts*, vol. 77 (1972), #33,867f.
Montanari, F., et al., *Chemical Abstract*, vol. 51 (1957), #5695f.

*Primary Examiner*—Joseph E. Evans
*Assistant Examiner*—L. Hendriksen
*Attorney, Agent, or Firm*—Sprung, Horn, Kramer & Woods

[57] ABSTRACT

Acid halides and anhydrides of acids of the formula

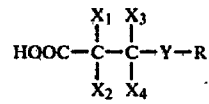

with the substituent definitions given in the description are obtained by reacting the corresponding acids with organic or inorganic acid halides or acid anhydrides. The new compounds are intermediate products for the preparation of new reactive dyestuffs.

5 Claims, No Drawings

CARBOXYLIC ACID DERIVATIVES

The present invention relates to acid halides and anhydrides of acids of the formula

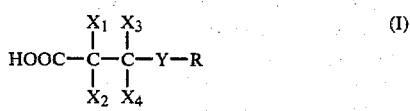

wherein $X_1$-$X_4$ = hydrogen or radicals which can be split off as anions, at least one of these radicals being a radical which can be split off as an anion, $Y = SO$ or $SO_2$ and $R$ = alkyl, aralkyl, aryl or hetaryl.

Preferred derivatives of (I) are the acid chlorides, acid bromides and acid fluorides, in particular those of compounds (I) in which at least one radical $X_1$-$X_4$ represents halogen, and the corresponding acid anhydrides.

Those acid halides in which $Y = SO_2$ and those in which $X_2$ and $X_4 = H$ and one of the radicals $X_1$ or $X_3 = Cl$ or Br and the other radical $X_1$ or $X_3 = H$ are particularly preferred.

The anhydrides of the acids on which the preferred acid halides are based are also preferred.

Alkyl groups are understood, in particular, as those which have 1-4 C atoms and can optionally contain substituents, for example halogen, such as Cl and Br, OH and CN. Aryl groups are understood, in particular, as phenyl radicals which optionally contain substituents, for example halogen, such as Cl and Br, $C_1$-$C_4$-alkyl, $C_1$-$C_4$-alkoxy, $C_1$-$C_4$-alkylsulphonyl, $NO_2$, CN, $CF_3$, $SO_3H$ and COOH.

Aralkyl radicals are understood, in particular, as benzyl radicals, which can optionally contain the substituents mentioned for the phenyl radicals.

The new derivatives of (I) are prepared in a manner which is in itself known, by reacting the known acids (I) with organic or inorganic acid halides or acid anhydrides at about 0°-150° C., preferably 10°-120° C.

Examples of suitable acid halides are sulphuryl chloride, thionyl halides, such as thionyl chloride, phosphorus halides, such as phosphorus tribromide and phosphorus oxychloride, and phosgene, and also carboxylic acid chlorides, such as benzoyl chloride, sulphonic acid chlorides, such as toluenesulphonyl chloride, and halogenated heterocyclic compounds, such as trifluorotriazine.

Examples of suitable acid anhydrides are the aliphatic or aromatic mono- or di-carboxylic acid anhydrides, such as acetic anhydride and phthalic anhydride, and anhydrides of inorganic acids, such as phosphorus pentoxide.

The reaction is in general carried out with stoichiometric amounts, if appropriate in the presence of customary inert solvents. It is also possible, however, to use the reactants as the solvent.

The reaction can also be carried out in the presence of hydrogen halide acceptors, preferably in amounts of 0.01-0.9 mol per mol of (I).

The new compounds are intermediate products, for example for the preparation of new reactive dyestuffs, which are obtained in the customary manner by reaction with appropriate dyestuffs containing amino groups.

EXAMPLE 1

248.5 g (1 mol) of dry 2-chloro-3-phenylsulphonylpropionic acid are suspended in 300 ml of thionyl chloride at 20° C. The suspension is warmed slowly to 60° C. After about 7 hours, the evolution of gas has ended. The excess thionyl chloride is distilled off, under reduced pressure at 240°-60° C., from the clear solution formed. The residue consists of 2-chloro-3-phenylsulphonylpropionyl chloride, which crystallises out on cooling. The yield is quantitative. The product has the following $^1$H-NMR spectrum; measured in deuterochloroform: $\delta = 3.83$ (multiplet, 2H), 4.93 (double doublet, 1H) and 7.50-8.10 (multiplet, 5H). When recrystallised from toluene, the compound has a melting point of 49° C.

EXAMPLE 2

293 g (1 mol) of dry 2-bromo-3-phenylsulphonylpropionic acid are suspended in 350 ml of thionyl chloride at 20° C. 2 ml of dimethylformamide are added and the suspension is warmed slowly to 60° C. After about 2 hours, the evolution of gas has ended. The excess thionyl chloride is distilled off, under reduced pressure at 40°-60° C., from the clear solution formed. The residue consists of 2-bromo-3-phenylsulphonylpropionyl chloride, which crystallises out on cooling. The yield is quantitative. The product has the following $^1$H-NMR spectrum, measured in deuterochloroform: $\delta = 3.68$ (double doublet, 1H), 4.13 (triplet, 1H), 4.92 (double doublet, 1H) and 7.50-8.10 (multiplet, 5H).

When recrystallised from toluene, the compound has a melting point of 47° C.

EXAMPLE 3

305 g (1 mol) of moist 3-chloro-3-phenylsulphonylpropionic acid are suspended in 350 ml of chlorobenzene. The water is removed from the mixture azeotropically, the mixture is cooled to 20°-30° C., 150 g of thionyl chloride are added and the mixture is warmed slowly to 60° C. When the evolution of gas has ended, the excess thionyl chloride and the solvent are distilled off under reduced pressure at 40°-60° C. The residue consists of 3-chloro-3-phenylsulphonylpropionyl chloride, which already partly crystallises out during the distillation. The yield is quantitative.

The product has the following $^1$H-NMR spectrum, measured in deuterochloroform: $\delta = 3.42$ (multiplet, 1H), 4.08 (double doublet, 1H), 5.12 (double doublet, 1H) and 7.40-8.20 (multiplet, 5H).

When recrystallised from chlorobenzene, the compound has a melting point of 99° C.

If, instead of the chlorine derivative, 3-bromo-3-phenylsulphonylpropionic acid is used and the procedure followed is as indicated above, 3-bromo-3-phenylsulphonylpropionyl chloride is obtained, also in quantitative yield $^1$H-NMR (DCCl$_3$): $\delta = 3.50$ (double doublet, 1H), 4.17 (double doublet, 1H), 5.16 (double doublet, 1H) and 7.40-8.15 (multiplet, 5H). Melting point, when recrystallised from toluene: 96° C.

EXAMPLE 4

283 g (1 mol) of dry 2,2-dichloro-3-phenylsulphonylpropionic acid are suspended in 400 ml of thionyl chloride at 20° C. 2 ml of dimethylformamide are added and the mixture is warmed slowly to 70°-75° C. After 4 hours, the evolution of gas has ended. The excess thionyl chloride is distilled off, under reduced pressure at 40°-60° C., from the clear solution formed. The residue consists of 2,2-dichloro-3-phenylsulphonylpropionyl chloride. The yield is quantitative.

The acid chloride has the following $^1$H-NMR spectrum (CCl$_4$): $\delta$=4.38 (singlet, 2H) and 7.40–8.10 (multiplet, 5H).

When recrystallised from toluene, the compound has a melting point of 57° C.

We claim:

1. An acid halide or anhydride of an acid of the formula:

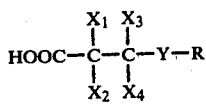

wherein
- $X_1$ to $X_4$ is independently hydrogen or halogen, at least one of these radicals being a halogen radical,
- Y equals SO$_2$, and
- R equals C$_1$–C$_4$ alkyl or phenyl.

2. An acid halide or acid anhydride of an acid according to claim 1 wherein $X_2$ and $X_4$ equals hydrogen.

3. An acid halide or acid anhydride of an acid according to claim 1 in which $X_2$ and $X_4$ are hydrogen and one of the radicals $X_1$ or $X_3$ is chlorine or bromine and the other radical $X_1$ or $X_3$ is hydrogen.

4. An acid halide or acid anhydride of an acid according to claim 1 in which $X_2$, $X_3$ and $X_4$ are hydrogen and $X_1$ is chlorine or bromine.

5. An acid halide or acid anhydride of an acid according to claim 1 in which $X_1$, $X_2$ and $X_4$ are hydrogen and $X_3$ is chlorine or bromine.

* * * * *